(12) United States Patent
Ramzipoor et al.

(10) Patent No.: US 7,255,707 B2
(45) Date of Patent: *Aug. 14, 2007

(54) INTRAVASCULAR DEVICE DEPLOYMENT MECHANISM INCORPORATING MECHANICAL DETACHMENT

(75) Inventors: Kamal Ramzipoor, Fremont, CA (US); Tom Holdych, Campbell, CA (US)

(73) Assignee: Micrus Endovascular Corporation, San Jose, CA (US)

( * ) Notice: Subject to any disclaimer, the term of this patent is extended or adjusted under 35 U.S.C. 154(b) by 342 days.

This patent is subject to a terminal disclaimer.

(21) Appl. No.: 11/020,810

(22) Filed: Dec. 22, 2004

(65) Prior Publication Data

US 2005/0113863 A1    May 26, 2005

Related U.S. Application Data

(63) Continuation of application No. 10/113,781, filed on Apr. 1, 2002, now Pat. No. 6,835,185, which is a continuation of application No. 09/501,466, filed on Feb. 9, 2000, now Pat. No. 6,478,773, which is a continuation of application No. 09/218,117, filed on Dec. 21, 1998, now Pat. No. 6,296,622.

(51) Int. Cl.
*A61M 29/00* (2006.01)

(52) U.S. Cl. .................................... 606/200
(58) Field of Classification Search ............... 606/108, 606/144, 151, 191–194, 200, 213; 623/1.11, 623/1.23
See application file for complete search history.

(56) References Cited

U.S. PATENT DOCUMENTS

| | | | |
|---|---|---|---|
| 1,341,052 A | 5/1920 | Gale | |
| 2,078,182 A | 4/1937 | MacFarland et al. | |
| 2,549,335 A | 4/1951 | Rahthus | |
| 3,334,629 A | 8/1967 | Cohn | |
| 3,485,234 A | 12/1969 | Stevens | |
| 3,649,224 A | 3/1972 | Anderson et al. | |
| 3,868,956 A | 3/1975 | Alfidi et al. | |
| 4,327,734 A | 5/1982 | White, Jr. | |
| 4,341,218 A | 7/1982 | Ü | |
| 4,346,712 A | 8/1982 | Handa et al. | |
| 4,402,319 A | 9/1983 | Handa et al. | |
| 4,441,495 A | 4/1984 | Hicswa | |
| 4,494,531 A | 1/1985 | Gianturco | |
| 4,512,338 A | 4/1985 | Balko et al. | |
| 4,545,367 A | 10/1985 | Tucci | |
| 4,553,545 A | 11/1985 | Maass et al. | |
| 4,611,594 A | 9/1986 | Grayhack et al. | |
| 4,629,458 A | 12/1986 | Pinchuk | |
| 4,638,803 A | 1/1987 | Rand | |
| RE32,348 E | 2/1987 | Pevsner | |
| 4,655,771 A | 4/1987 | Wallsten | |

(Continued)

*Primary Examiner*—Anhtuan T. Nguyen
*Assistant Examiner*—Melanie Tyson
(74) *Attorney, Agent, or Firm*—Fulwider Patton LLP

(57) ABSTRACT

The apparatus for deployment of a therapeutic device such as a micro-coil detachably mounts the therapeutic device to a distal portion of a pusher member. In one embodiment, the therapeutic device is detachably mounted to the distal portion of the pusher member by a connector fiber for securing the therapeutic device to the pusher member. The connector fiber passes through a cutter member such as a cutting ring within the distal portion of the pusher member, for cutting the connector fiber to release the therapeutic device when a desired placement of the therapeutic device within the vasculature is achieved.

4 Claims, 2 Drawing Sheets

U.S. PATENT DOCUMENTS

| | | | |
|---|---|---|---|
| 4,670,286 A | 6/1987 | Nyilas et al. |
| 4,718,907 A | 1/1988 | Karwoski et al. |
| 4,748,986 A | 6/1988 | Morrison et al. |
| 4,768,507 A | 9/1988 | Fischell et al. |
| 4,795,458 A | 1/1989 | Regan |
| 4,800,882 A | 1/1989 | Gianturco |
| 4,813,925 A | 3/1989 | Anderson, Jr. et al. |
| 4,856,516 A | 8/1989 | Hillstead |
| 4,944,746 A | 7/1990 | Iwata et al. |
| 4,957,479 A | 9/1990 | Roemer |
| 4,990,155 A | 2/1991 | Wilkoff |
| 5,002,556 A | 3/1991 | Ishida et al. |
| 5,015,253 A | 5/1991 | MacGregor |
| 5,019,090 A | 5/1991 | Pinchuk |
| 5,026,377 A | 6/1991 | Burton et al. |
| 5,035,706 A | 7/1991 | Giantureo et al. |
| 5,037,377 A | 8/1991 | Alonso |
| 5,041,084 A | 8/1991 | DeVries et al. |
| 5,041,126 A | 8/1991 | Gianturco |
| 5,061,275 A | 10/1991 | Wallsten et al. |
| 5,064,435 A | 11/1991 | Porter |
| 5,071,407 A | 12/1991 | Termin et al. |
| 5,104,404 A | 4/1992 | Wolff |
| 5,108,407 A | 4/1992 | Geremia et al. |
| 5,109,867 A | 5/1992 | Twyford, Jr. |
| 5,122,137 A | 6/1992 | Lennox |
| 5,133,364 A | 7/1992 | Palermo et al. |
| 5,133,731 A | 7/1992 | Butler et al. |
| 5,133,732 A | 7/1992 | Wiktor |
| 5,141,502 A | 8/1992 | Macaluso, Jr. |
| 5,143,085 A | 9/1992 | Wilson |
| 5,147,370 A | 9/1992 | McNamara et al. |
| 5,151,105 A | 9/1992 | Kwan-Gett |
| 5,152,784 A | 10/1992 | Tsilibary |
| 5,160,341 A | 11/1992 | Brenneman et al. |
| 5,171,273 A | 12/1992 | Silver et al. |
| 5,176,625 A | 1/1993 | Brisson |
| 5,176,661 A | 1/1993 | Evard et al. |
| 5,181,921 A | 1/1993 | Makita et al. |
| 5,183,085 A | 2/1993 | Timmermans |
| 5,186,992 A | 2/1993 | Kite, III |
| 5,188,621 A | 2/1993 | Samson |
| 5,192,290 A | 3/1993 | Hilal |
| 5,197,977 A | 3/1993 | Hoffman, Jr. et al. |
| 5,203,772 A | 4/1993 | Hammerslag et al. |
| 5,211,658 A | 5/1993 | Clouse |
| 5,217,484 A | 6/1993 | Marks |
| 5,222,970 A | 6/1993 | Reeves |
| 5,224,953 A | 7/1993 | Morgentaler |
| 5,228,453 A | 7/1993 | Sepetka |
| 5,238,004 A | 8/1993 | Sahatjian et al. |
| 5,250,071 A | 10/1993 | Palermo |
| 5,275,173 A | 1/1994 | Samson et al. |
| 5,304,194 A | 4/1994 | Chee et al. |
| 5,304,198 A | 4/1994 | Samson |
| 5,312,415 A | 5/1994 | Palermo |
| 5,314,472 A | 5/1994 | Fontaine |
| 5,322,501 A | 6/1994 | Mahmud-Durrani |
| 5,336,205 A | 8/1994 | Zenzen et al. |
| 5,341,818 A | 8/1994 | Abrams et al. |
| 5,342,387 A | 8/1994 | Summers |
| 5,350,397 A | 9/1994 | Palermo et al. |
| 5,354,295 A | 10/1994 | Guglielmi et al. |
| 5,354,309 A | 10/1994 | Schnepp-Pesch et al. |
| 5,368,049 A | 11/1994 | Raman et al. |
| 5,373,856 A | 12/1994 | Grenouillet |
| 5,382,259 A | 1/1995 | Phelps et al. |
| 5,383,887 A | 1/1995 | Nadal |
| 5,395,390 A | 3/1995 | Simon et al. |
| 5,405,377 A | 4/1995 | Cragg |
| 5,411,475 A | 5/1995 | Atala et al. |
| 5,415,664 A | 5/1995 | Pinchuk |
| 5,417,708 A | 5/1995 | Hall et al. |
| 5,423,829 A | 6/1995 | Pham et al. |
| 5,433,723 A | 7/1995 | Lindenberg et al. |
| 5,441,516 A | 8/1995 | Wang et al. |
| 5,443,478 A | 8/1995 | Purdy |
| 5,443,498 A | 8/1995 | Fontaine |
| 5,484,449 A | 1/1996 | Amundson et al. |
| 5,514,115 A | 5/1996 | Frantzen et al. |
| 5,514,176 A | 5/1996 | Bosley, Jr. |
| 5,520,194 A | 5/1996 | Miyata et al. |
| 5,522,822 A | 6/1996 | Phelps et al. |
| 5,522,836 A | 6/1996 | Palermo |
| 5,523,092 A | 6/1996 | Hanson et al. |
| 5,527,336 A | 6/1996 | Rosenbluth et al. |
| 5,540,701 A | 7/1996 | Sharkey et al. |
| 5,549,624 A | 8/1996 | Mirigian et al. |
| 5,562,641 A | 10/1996 | Flomenblit et al. |
| 5,562,698 A | 10/1996 | Parker |
| 5,569,245 A | 10/1996 | Guglielmi et al. |
| 5,578,074 A | 11/1996 | Mirigian |
| 5,582,619 A | 12/1996 | Ken |
| 5,603,694 A | 2/1997 | Brown et al. |
| 5,607,445 A | 3/1997 | Summers |
| 5,609,627 A | 3/1997 | Goicoechea et al. |
| 5,613,981 A | 3/1997 | Boyle et al. |
| 5,624,461 A | 4/1997 | Mariant |
| 5,637,113 A | 6/1997 | Tartaglia et al. |
| 5,638,827 A | 6/1997 | Palmer et al. |
| 5,639,277 A | 6/1997 | Mariant et al. |
| 5,643,254 A | 7/1997 | Scheldrup et al. |
| 5,645,564 A | 7/1997 | Northrup et al. |
| 5,649,949 A | 7/1997 | Wallace et al. |
| 5,653,726 A | 8/1997 | Kieturakis |
| 5,667,522 A | 9/1997 | Flomenblit et al. |
| 5,676,697 A | 10/1997 | McDonald |
| 5,690,671 A | 11/1997 | McGurk et al. |
| 5,693,085 A | 12/1997 | Buirge et al. |
| 5,702,373 A | 12/1997 | Samson |
| 5,702,414 A | 12/1997 | Richter et al. |
| 5,713,907 A | 2/1998 | Hogendijk et al. |
| 5,722,989 A | 3/1998 | Fitch et al. |
| 5,725,546 A | 3/1998 | Samson |
| 5,733,329 A | 3/1998 | Wallace et al. |
| 5,743,905 A | 4/1998 | Eder et al. |
| 5,746,765 A | 5/1998 | Kleshinski et al. |
| 5,746,769 A | 5/1998 | Ton et al. |
| 5,749,883 A | 5/1998 | Halpern |
| 5,749,891 A | 5/1998 | Ken et al. |
| 5,749,894 A | 5/1998 | Engelson |
| 5,749,918 A | 5/1998 | Hogendijk et al. |
| 5,749,921 A | 5/1998 | Lenker et al. |
| 5,759,161 A | 6/1998 | Ogawa et al. |
| 5,788,653 A | 8/1998 | Lorenzo |
| 5,797,957 A | 8/1998 | Palmer et al. |
| 5,800,455 A | 9/1998 | Palermo et al. |
| 5,800,526 A | 9/1998 | Anderson et al. |
| 5,814,062 A | 9/1998 | Sepetka et al. |
| 5,824,059 A | 10/1998 | Wijay |
| 5,947,963 A | 9/1999 | Guglielmi |
| 5,984,929 A | 11/1999 | Bashiri et al. |
| 5,989,242 A | 11/1999 | Saadat et al. |
| 6,478,773 B1 | 11/2002 | Gandhi et al. |
| 6,835,185 B2 * | 12/2004 | Ramzipoor et al. ............ 604/57 |

* cited by examiner

INTRAVASCULAR DEVICE DEPLOYMENT MECHANISM INCORPORATING MECHANICAL DETACHMENT

RELATED APPLICATIONS

This is a continuation of application Ser. No. 10/113,781, filed 1 Apr. 2002, now Pat. No. 6,835,185, which is a continuation-in-part of application Ser. No. 09/501,466, filed 9 Feb. 2000, now Pat. No. 6,478,773, which is a continuation-in-part of application Ser. No. 09/218,117, filed 21 Dec. 1998, now Pat. No. 6,296,622.

BACKGROUND OF THE INVENTION

1. Field of the Invention

This invention relates generally to devices for interventional therapeutic treatment or vascular surgery for treatment of defects in the vasculature, and more particularly concerns a system and method for delivering intravascular interventional devices, such as for treatment of aneurysms.

2. Description of Related Art

Vascular interventional devices such as vasoocclusive devices are typically placed within the vasculature of the human body by use of a catheter. Vascular interventional devices such as stents can be placed within an occluded vessel to facilitate blood flow through the vessel, and vasoocclusive devices are typically either placed within a blood vessel to block the flow of blood through a vessel making up that portion of the vasculature through the formation of an embolus, or are placed within an aneurysm stemming from the vessel to form such an embolus within the aneurysm. Stents can have a wide variety of configurations, but generally need to be placed and then released at a desired location within a blood vessel. Vasoocclusive devices used for these procedures can also have a wide variety of configurations, and aneurysms have been treated with external surgically placed clips, detachable vasoocclusive balloons and embolus generating vasoocclusive devices such as one or more vasoocclusive coils.

The delivery of such vasoocclusive devices have typically been accomplished by a variety of means, including via a catheter in which the device is pushed through an opening at the distal end of the catheter by a pusher to deploy the device. The vasoocclusive devices can be produced in such a way that they will pass through the lumen of a catheter in a linear shape and take on a complex shape as originally formed after being deployed into the area of interest, such as an aneurysm.

One conventional releasable balloon catheter used to embolize vascular lesions has a tube portion made of a material such as a hydrophilic polymer, located between the catheter and the balloon, that can be melted by heating the tube, or can be dissolved in the blood when heated, and electrodes are provided for heating the tube. Another conventional technique for separating a balloon from a balloon catheter involves the melting and breaking of a connecting member between the balloon and the catheter body, when power is supplied to electrodes provided for heating the connecting member. When the connecting member is heated to temperatures of about 70° C. and slight tension is applied, the balloon can be separated from the main catheter body.

An implant delivery assembly is also known that is used for delivery of implants such as embolic coils, utilizing a shape memory decoupling mechanism activated when exposed to body temperature. A cooling solution is flushed through the catheter during introduction and placement of the implant in order to prevent premature release of the implant prior to the time that the implant is to be released. Another implant delivery assembly includes an electrical heating system for heating the coupling mechanism to a temperature at which the shape memory material returns to its original shape, to deploy the implant.

Another device is known in which a device to be implanted is detached by application of a high-frequency current which melts and severs a resin that is used to retain the device to be implanted until the device is to be deployed. In another known device, an electrolytically severable link is dissolved by activation of a power source electrically coupled to the electrolytically severable link to detach the device to be implanted.

In another conventional technique, a conductive guidewire delivers a high frequency current through the guidewire to melt and sever a joint to detach an implanted device from the guidewire. The patient is grounded during the procedure, and current is introduced via the guidewire, rather than with a two way current path.

Such devices that release the interventional device by melting or dissolving the intermediate section between the catheter tip and implanted device may cause thermal damage of surrounding tissues during detachment that can cause embolization in the bloodstream, and may also potentially release undesirable particles of materials into the bloodstream that can also cause embolization in the bloodstream. There is therefore a need for a precise method of deploying therapeutic interventional devices without compromising the position of the implant, without causing thermal damage to surrounding tissues, and without releasing undesirable particles of materials into the bloodstream and risking the formation of emboli in the bloodstream. The present invention meets these and other needs.

SUMMARY OF THE INVENTION

Briefly, and in general terms, the present invention provides for an apparatus for deployment of a therapeutic device such as a micro-coil using a catheter by connecting the therapeutic device to a distal portion of a pusher member. In one presently preferred embodiment, the therapeutic device is detachably mounted to the distal portion of the pusher member by a connector thread or fiber passing through a cutter member that can be pulled proximally for cutting the connector fiber to release the therapeutic device. In one presently preferred aspect, the cutter member is advantageously contained substantially within the distal portion of the pusher member, and since the connecting fiber is cut at a location fully contained within the distal portion of the pusher member, the potential for releasing undesirable particles of materials into the bloodstream and consequent embolization in the bloodstream is virtually eliminated.

The invention accordingly provides for an apparatus for release and deployment of a therapeutic device within the vasculature of a patient, which comprises an elongated, flexible pusher member having an interior lumen, and a connector fiber detachably mounting the therapeutic device to the pusher member for placement of the therapeutic device within the vasculature, the connector fiber being capable of being broken by a cutter member. The cutter member is disposed at the distal end of an elongated pull member adjacent to the connector fiber, so that the cutter member can be pulled proximally by the elongated pull member for cutting the connector fiber to cause the connector fiber to break and release the therapeutic device for detaching and deploying the therapeutic device from the flexible pusher member when a desired placement of the therapeutic device within the vasculature is achieved. In one currently preferred aspect, the distal portion of the pusher member includes at least one entry port communicating with the interior lumen, with the cutter member disposed in the interior lumen of the pusher member adjacent to one or more entry ports. In another presently preferred aspect, the connector fiber passes through the cutter member. In a currently preferred embodiment, the cutter member comprises a cutting ring, with the cutter member connected to the distal end of the elongated pull member, such as a pull wire. In presently preferred aspects of the apparatus, the connector fiber is formed from a plastic material, such as polyethylene.

In one presently preferred embodiment, the therapeutic device to be placed within the vasculature of a patient is connected to an annular connector ring, and the connector fiber mounting the therapeutic device to the pusher member passes through the connector ring to secure the therapeutic device to the pusher member. In a currently preferred aspect, the connector fiber extends from a proximal portion of the pusher member to form a loop through the connector ring, and back through the one or more ports through the pusher member to the proximal portion of the pusher member. In another presently preferred aspect, the therapeutic device comprises a vasoocclusive device, such as a microcoil.

The invention also provides for a method for release and deployment of a therapeutic device within the vasculature of a patient. In the method of the invention, a therapeutic device to be placed within the vasculature of a patient is provided; and an elongated, flexible pusher member. A connector fiber detachably mounts the therapeutic device to the pusher member for placement of the therapeutic device within the vasculature, with the connector fiber being capable of being broken by cutting, and the therapeutic device is positioned at a desired placement within a patient's vasculature. Thereafter, a portion of the connector fiber is cut by a cutter member disposed at the distal end of an elongated pull member, by pulling the pull member proximally, for detaching and deploying the therapeutic device from the flexible pusher member when a desired placement of the therapeutic device within a patient's vasculature is achieved. In a presently preferred aspect of the method, the portion of the connector fiber to be cut is passed through a cutting ring at the distal end of a pull member such as a pull wire, the cutting ring being disposed within the lumen of the flexible pusher member, and the connector fiber is cut by pulling the pull wire proximally so that the cutting ring breaks the connector fiber.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
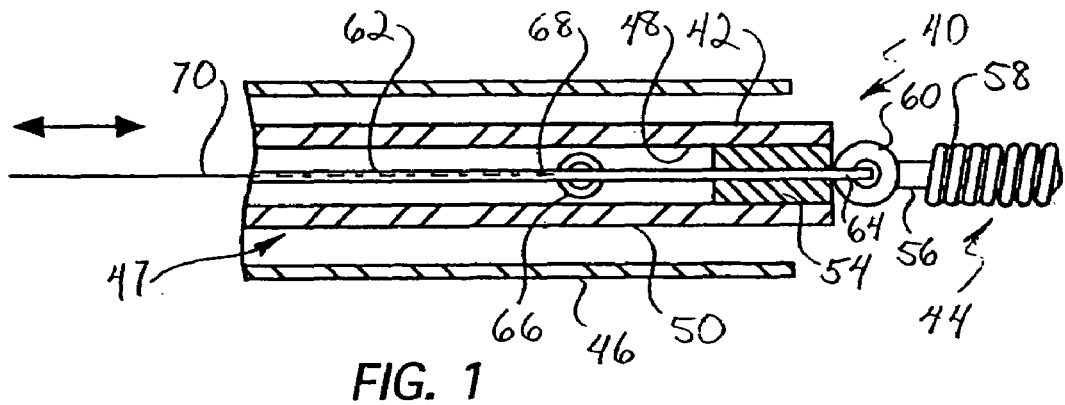
FIG. 1 is a top sectional view of a preferred embodiment of the apparatus for release and deployment of a therapeutic device.

As is illustrated in the drawings, in a first presently preferred embodiment, the invention is embodied in an apparatus for deployment of a therapeutic device such as a micro-coil using a catheter by connecting the therapeutic device to a distal portion of a pusher member by a connector fiber that can be broken by movement of a cutter member through which the connector fiber passes, to break the connector fiber and thereby release the therapeutic device for placement in the vasculature.

Figure 2:
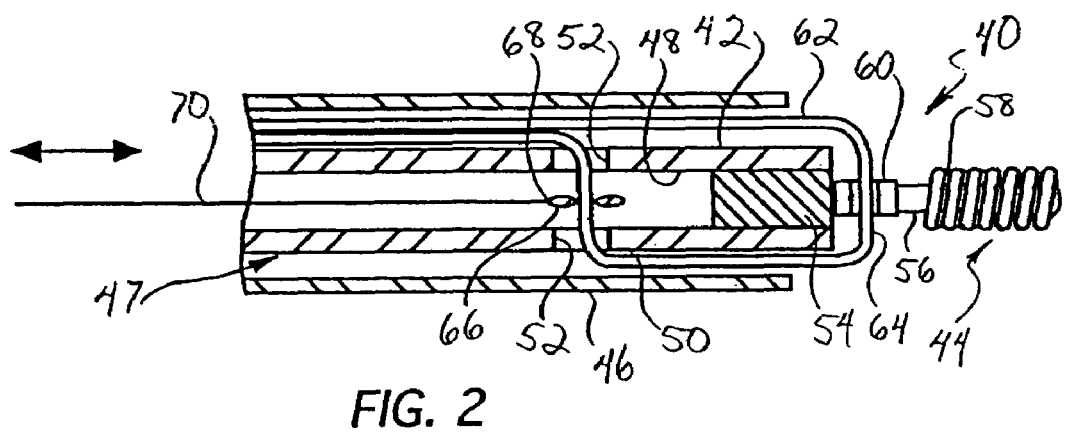
FIG. 2 is a side sectional view of the apparatus of FIG. 1.
Figure 3:
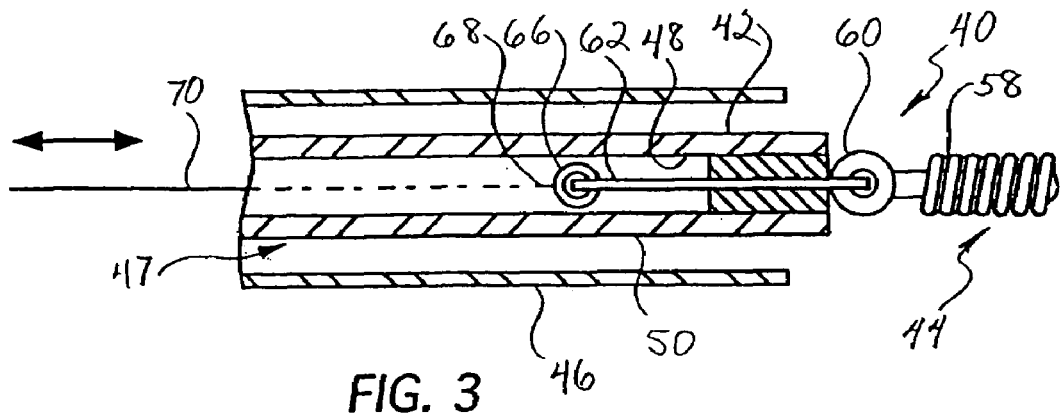
FIG. 3 is a bottom sectional view of the apparatus of FIG. 1.
Figure 4:
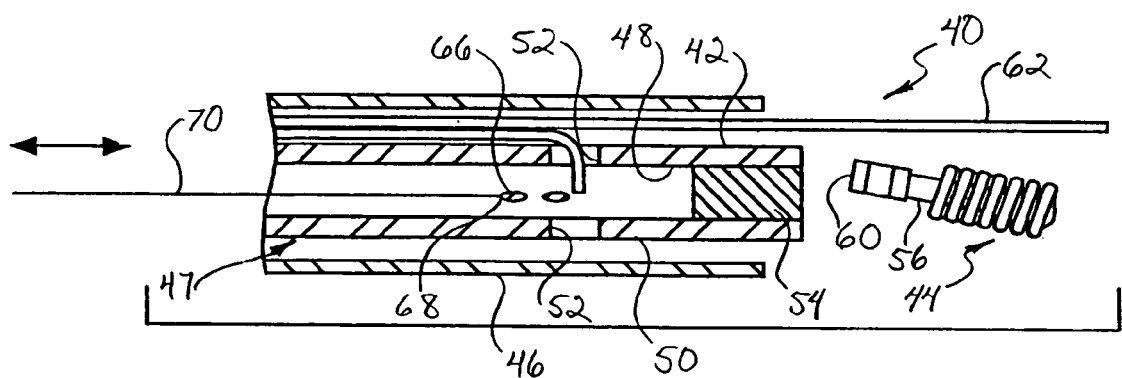
FIG. 4 is a side sectional view of the apparatus of FIG. 1, illustrating release of the therapeutic device upon cutting of the elongated connector fiber.

With reference to FIGS. 1-4, in a presently preferred embodiment, the invention provides for an apparatus 40 including an elongated, flexible pusher member 42 for release and deployment of a therapeutic device 44 such as a vasoocclusive device, which may for example be a micro-coil, only a portion of which is shown, within the vasculature of a patient, through a delivery catheter 46. The pusher member has a shaft 47 that typically has an outer diameter of approximately 0.015", and an inside diameter of approximately 0.007, and can be formed from polyethylene terephthalate (PET) tubing. The pusher member has a distal portion 50 with entry ports 52 in communication with the interior lumen 48, and a plug 54 at the distal end of the pusher member, typically secured within the distal end of the pusher member by adhesive, such as a cyanoacrylate adhesive, for example.

The therapeutic device is typically connected to a stem 56 such as by solder 58, although the therapeutic device may also be connected to the stem by other adhesive materials such as a liquid polyimide adhesive material, for example, and the stem is in turn connected to an annular connector ring 60, typically by an adhesive such as a cyanoacrylate adhesive, for example. The therapeutic device and connector ring may also be covered with a polyimide coating for improved insulation of the therapeutic device and connector ring. The therapeutic device is mounted and secured to the distal portion of the pusher member by an elongated connector thread or fiber 62 extending from a proximal portion of the pusher member to form a loop 64 through the connector ring, and extending back through the entry ports of the pusher member to the proximal portion of the pusher member. In a presently preferred embodiment, the connector fiber is formed of polyethylene, and is typically about 0.015 to 0.030 inches in diameter, although the connector fiber can be as thin as about 0.0005 inches in diameter, and can be formed from a variety of plastic materials with high tensile strength and that can be cut by a suitable application of shear forces. Proximal ends of the connector fiber maybe secured to a proximal portion of the shaft by one or more PET rings, and may be twisted together, and may also be secured to the proximal portion of the shaft by adhesive, such as a UV cured adhesive, for example.

A portion of the connector fiber to be broken to deploy the therapeutic device passes through a cutter member 66, such as a cutting ring, for example. The cutter member is preferably contained substantially within the distal portion of the pusher member, and since the connecting fiber is cut at a location fully contained within the distal portion of the pusher member, the potential for releasing undesirable particles of materials into the bloodstream and consequent embolization in the bloodstream is virtually eliminated. The cutter member is preferably connected to the distal end 68 of an elongated pull member 70, such as a pull wire, thread, cable or fiber. The connector fiber is an elongated member formed from a plastic material, and is preferably a high tensile plastic material, such as polyethylene, but may be formed of other similar materials that are preferably high tensile materials capable of being cut by application of appropriate shear forces. In operation of the method, the connector fiber detachably mounts the therapeutic device to the pusher member for placement of the therapeutic device within the vasculature, and the therapeutic device is positioned at a desired placement within a patient's vasculature. Thereafter, a portion of the connector fiber is cut by the cutter member by pulling the pull member proximally, for detaching and deploying the therapeutic device from the flexible pusher member when a desired placement of the therapeutic device within a patient's vasculature is achieved.

In a presently preferred aspect of the method, the portion of the connector fiber to be cut is passed through a cutting ring at the distal end of a pull member, such as a pull wire, and the cutting ring is disposed within the lumen of the flexible pusher member. The connector fiber is cut by pulling the pull wire proximally so that the cutting ring breaks the connector fiber.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An apparatus for release and deployment of a therapeutic device having an annular connector ring within the vasculature of a patient, comprising:
    an elongated, flexible pusher member;
    a connector fiber connected to the elongated, flexible pusher member and forming a loop through the connector ring of the therapeutic device to detachably mount the therapeutic device to the pusher member for placement of the therapeutic device within the vasculature;
    a cutter member disposed adjacent to the connector fiber, the cutter member having an elongated pull member connected to the cutter member to allow a user to move the cutter member for cutting the connector fiber to cause the connector fiber to break and release the therapeutic device.

2. The apparatus of claim 1, wherein said connector fiber is formed from a plastic material.

3. The apparatus of claim 1, wherein said connector fiber is formed from polyethylene.

4. The apparatus of claim 1, wherein said pusher member comprises an interior lumen and at least one entry port communicating with said interior lumen, and said cutter member is disposed in the interior lumen adjacent to said at least one entry port.

* * * * *